United States Patent
Montorsi et al.

(10) Patent No.: US 8,841,283 B2
(45) Date of Patent: Sep. 23, 2014

(54) METHODS FOR THE PREPARATION OF DROSPIRENONE AND INTERMEDIATES THEREOF

(75) Inventors: Mauro Montorsi, Milan (IT); Edoardo Mariani, Milan (IT); Luca Gambarin, Milan (IT); Gianmauro Orru', Milan (IT); Romeo Scalaprice, Milan (IT); Massimo Merlo, Milan (IT); Erika Andriolo, Milan (IT)

(73) Assignee: Newchem S.p.A., Milan (IT)

( * ) Notice: Subject to any disclaimer, the term of this patent is extended or adjusted under 35 U.S.C. 154(b) by 58 days.

(21) Appl. No.: 13/813,195

(22) PCT Filed: Jul. 22, 2011

(86) PCT No.: PCT/EP2011/062651
§ 371 (c)(1),
(2), (4) Date: Jan. 30, 2013

(87) PCT Pub. No.: WO2012/016860
PCT Pub. Date: Feb. 9, 2012

(65) Prior Publication Data
US 2013/0131335 A1    May 23, 2013

(30) Foreign Application Priority Data
Aug. 3, 2010  (EP) .................................... 10171743

(51) Int. Cl.
*A61K 31/34* (2006.01)
*C07D 307/94* (2006.01)
*C07J 21/00* (2006.01)
*C07J 53/00* (2006.01)

(52) U.S. Cl.
CPC ............. *C07J 21/003* (2013.01); *C07D 307/94* (2013.01); *A61K 31/34* (2013.01); *C07J 53/008* (2013.01)
USPC .......................................... 514/173; 540/15

(58) Field of Classification Search
CPC .............................. A61K 31/34; C07D 307/94
USPC .......................................... 514/173; 540/15
See application file for complete search history.

(56) References Cited

U.S. PATENT DOCUMENTS

| | | |
|---|---|---|
| 2006/0264412 A1 | 11/2006 | Franczyk, II et al. |
| 2008/0207575 A1 | 8/2008 | Costantino et al. |
| 2009/0023914 A1 | 1/2009 | Pontiroli et al. |
| 2010/0222571 A1 | 9/2010 | Andriolo et al. |
| 2010/0261896 A1 | 10/2010 | Nickisch et al. |
| 2010/0331291 A1 | 12/2010 | Costantino et al. |
| 2011/0144363 A1 | 6/2011 | Iglesias et al. |

OTHER PUBLICATIONS

Li, Weipeng, "Method for Synthesizing Drospirenone and Its Intermediate", XP002634378 2010.
Li, Weipeng, "Method for Synthesizing Drospirenone and Its Intermediate", XP002634379 & CN 101 775 057 A (Zhejiang Xianju Pharm Co Ltd) 2010.
CN 101 830 959 A (Hangzhou Longshan Chemical Co Ltd) 2010, XP002634380.
CN 101 830 959 A (Hangzhou Longshan Chemical Co Ltd) 2010, XP002634381.

*Primary Examiner* — Brenda Coleman
(74) *Attorney, Agent, or Firm* — Silvia Salvadori, P.C.

(57) ABSTRACT

The invention relates to a process for the preparation of Drospirenone in high yields and purity starting from a compound of formula 2

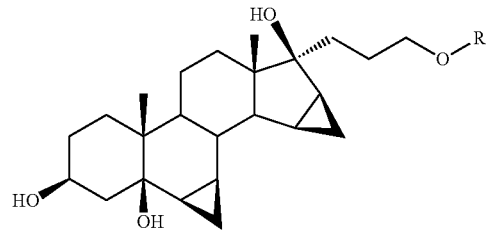

wherein R is a hydroxyl protective group as defined in the claims, through a sequence of oxidation, deprotection, lactonization and water elimination steps, and wherein the steps of oxidation and lactonization are performed with 1,3,5-trichloro1,3,5-triazine-2,4,6-(1H,3H,5H)-trione (trichloroisocyanuric acid, TCCA) or 1,3-dichloro-1,3,5-triazine-2,4,6-(1H,3H,5H)-trione (dichloroisocyanuric acid, DCCA) or an alkaline metal salt thereof such as the sodium salt dihydrate (DCCA sodium salt) or 1-hydroxy-1,2-benziodoxol-3(1H)-one 1-oxide (IBX). New synthetic intermediates useful for the synthesis of Drospirenone are disclosed, too.

15 Claims, No Drawings

METHODS FOR THE PREPARATION OF DROSPIRENONE AND INTERMEDIATES THEREOF

This application is a National Stage Entry under 35 U.S.C. 371 of PCT/EP2011/062651 filed Jul. 22, 2011, which claims priority to and the benefit of European Application No. 10171743.7, filed on Aug. 3, 2010, the contents of which are incorporated herein by reference.

The invention relates to a process for the preparation of Drospirenone and new synthetic intermediates thereof. The process involves efficient oxidizing agents which allow to avoid the use of heavy metals based-oxidants and to obtain Drospirenone in high yields and purity.

BACKGROUND OF THE INVENTION

Drospirenone is a synthetic progestin widely used in contraceptive therapy. Chemically known as 6β,7β,15β,16β-dimethylene-3-oxo-17α-pregn-4-ene-21,17-carbolactone, it has the following structural formula 5.

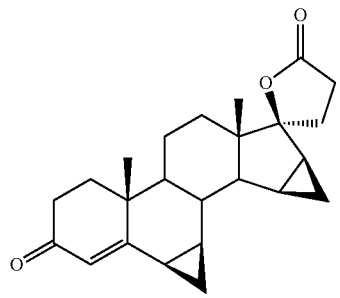

Several synthetic routes for the production of Drospirenone have been proposed so far, such as, for example, those disclosed in U.S. Pat. No. 6,121,465, WO2006/059168, WO2006/061309, U.S. Pat. No. 7,585,971B2, U.S. Pat. No. 7,319,154B2, U.S. Pat. No. 6,933,395, U.S. Pat. No. 4,416,985.

The oxidation processes reported in the prior art (WO2008/137050, U.S. Pat. No. 7,585,971B2, U.S. Pat. No. 7,319,154B2, EP075189, U.S. Pat. No. 6,933,395B1 and EP2019114A1) are performed starting from compound 3 or from a mixture of compound 3 and the epimers of lactol 8

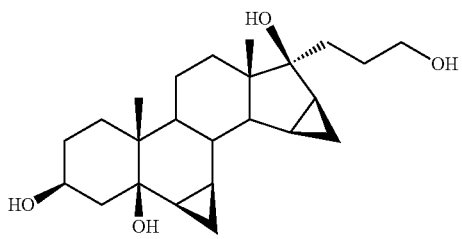

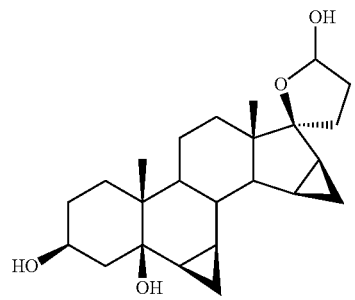

WO2008/137050 to Sicor describes the oxidation of intermediate 3 to Drospirenone using potassium permanganate.

The preparation of Drospirenone 5 by oxidation of intermediate 3 and/or the epimeric lactols 8 using reagents such as pyridine-$SO_3$ complex and TEMPO/calcium hypochlorite, potassium tert-butylate/cyclohexanone, manganese (IV) oxide, or N-methylmorpholine N-oxide (NMMO)/Tetrapropylammonium perruthenate (RAP) are disclosed in U.S. Pat. No. 7,585,971B2 to Industriale Chimica.

In U.S. Pat. No. 7,319,154B2 to Schering the oxidation of compound 3 to Drospirenone through the 3-oxo-lactone intermediate 4 using TEMPO/sodium hypochlorite allows to obtain Drospirenone 5 in 77% overall yield.

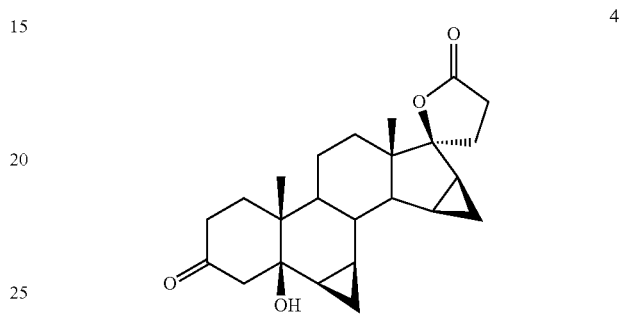

EP075189 to Schering discloses the oxidation of 3 to 5 using Cr(VI)$O_3$/Pyr in 56% overall yield.

U.S. Pat. No. 6,933,395B1 to Schering discloses overall yields of 65% for the oxidation of 3 to 5 using sodium bromate as oxidizing agent in the presence of ruthenium(III) chloride.

A two-step conversion of intermediate 3 protected at the primary hydroxyl group as the trimethylsilyl derivative compound 17α-[3-(trimethylsilanyloxy)propyl]-6β,7β,15β,16β-dimethyl en-5β-androstane-3β,5,17β-triol 2a) into Drospirenone 5 using 1-hydroxy-1,2-benziodoxol-3(1H)-one 1-oxide (2-iodoxybenzoic acid, IBX) followed by the Jones reagent is described in EP2019114A1 to Newchem. The conversion proceeds in 51% overall yield.

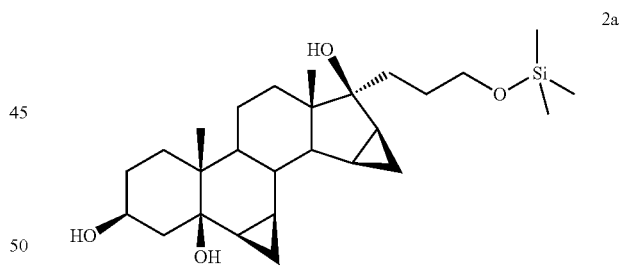

DESCRIPTION OF THE INVENTION

According to the process of the present invention, Drospirenone 5 is prepared starting from a compound of formula 2

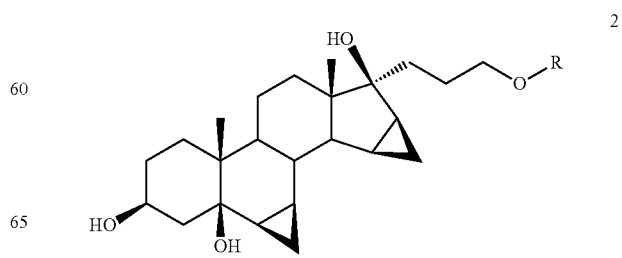

wherein R is a hydroxyl protective group selected from the group consisting of a silyl derivative. $Q_3Si—$, wherein each Q, independently from one another, represents $(C_1-C_6)$alkyl, $(C_6-C_{10})$aryl, $(C_1-C_4)$alkylaryl or $(C_1-C_4)$alkoxyaryl, through a sequence of oxidation, lactonization and water elimination steps, wherein the steps of oxidation and lactonization are performed with 1,3,5-trichloro-1,3,5-triazine-2,4,6-(1H,3H,5H)-trione (trichloroisocyanuric acid, TCCA), 1,3-dichloro-1,3,5-triazine-2,4,6-(1H,3H,5H)-trione (dichloroisocyanuric acid, DCCA) or an alkaline metal salt thereof such as the sodium salt dihydrate (dichloroisocyanuric acid sodium salt dihydrate, DCCA sodium salt dihydrate), or 1-hydroxy-1,2-benziodoxol-3(1H)-one 1-oxide (IBX).

In a first embodiment of the invention, the process involves the initial step of removal of the hydroxyl protecting group R from a compound of formula 2, followed by the steps of oxidation of the 3β-hydroxyl and of the primary hydroxyl in C-22 position with concomitant lactonization and final elimination of water from the C4-C5 positions to give Drospirenone 5.

In a second embodiment of the invention the process involves the removal of the hydroxyl protecting group R from a compound of formula 2 and the concomitant steps of oxidation of the 3β-hydroxyl and of the hydroxyl in C-22 position, lactonization and elimination of water to form directly Drospirenone 5.

In a third embodiment of the invention the process involves the sequential steps of oxidation of the 3β-hydroxyl group of compound 2, removal of the primary hydroxyl protective group, oxidation/lactonization and final elimination of water from the C4-C5 positions to give Drospirenone 5.

According to the first embodiment, the process for the preparation of Drospirenone 5 from a compound of formula 2 involves the following sequential steps: a)-c):

a) removal of the hydroxyl protective group of the compound of formula 2 as above defined to give 1.7α-(3-hydroxypropyl)-6β,7β,15β,16β-dimethylen-5β-androstane-3β,5,17β-triol of formula 3

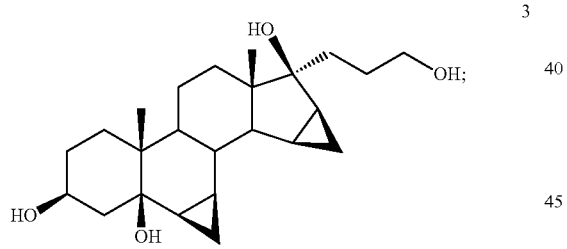

3 b) reaction of the compound of formula 3 with an oxidizing agent selected from TCCA in the presence of a base, or with IBX to give the compound of formula 4

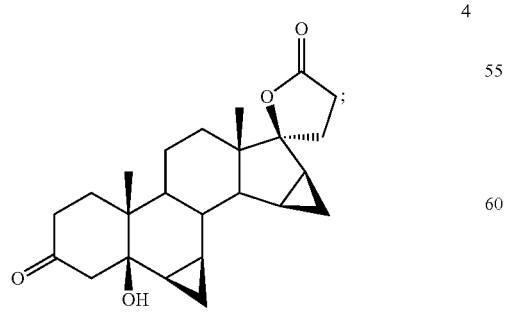

4 c) elimination of water from the positions C4-C5 of compound 4, whereby Drospirenone 5 is obtained.

The process according to the first embodiment is summarised in the following Scheme 1:

Scheme 1

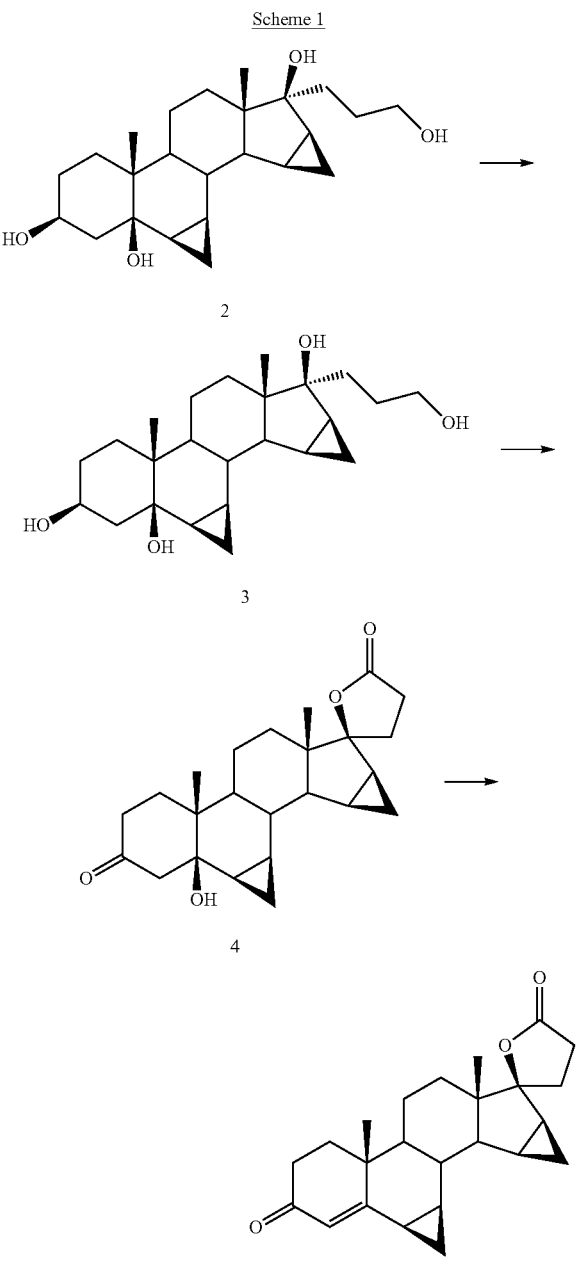

The compounds of formula 2 are known and can be prepared from 3β,5-dihydroxy-6β,7β,15β,16β-dimethylen-5β-androst-17-one 1 as described in EP2019114A1.

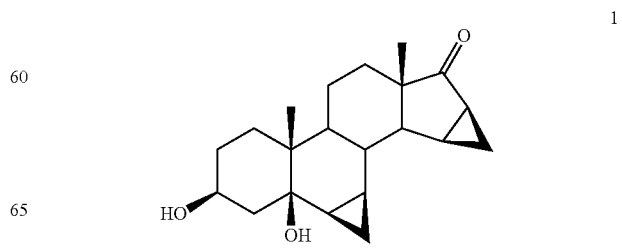

1

In the initial step a) compound 2 is deprotected to afford compound 3, i.e. 17α-(3-hydroxypropyl)-6β,7β,15β,16β-dimethylen-5β-androstane-3β,5,17β-triol.

When the R protective group in 2 is (CH$_3$)$_3$Si— (compound 2a), the deprotection, if desired, may take place during the work-up of the reaction from which 2a is obtained by 1, by contact of 2a with water, as described in Example 1.

When R is —Si(CH$_3$)$_2$[C(CH$_3$)$_3$] (compound 2b), the deprotection can be performed preferably by reaction of isolated 2b with tetrabutylammonium fluoride in tetrahydrofuran, analogously to the procedure described in Example 10.

In step b), compound 3 is oxidised to compound 4 by treatment with TCCA or IBX.

When the oxidant is represented by TCCA, the reaction is preferably performed in an organic solvent chosen from ketones, esters, amides, chlorinated solvents or mixtures thereof, at a temperature comprised between about 0° C. and about 70° C., using from 0.5 to 1.0, preferably 1.5, moles of TCCA for one mole of 3. The oxidation reaction is performed in the presence of a base, generally an amine. The base is preferably pyridine used in an amount of 1 to 8 moles for one mole of compound 3. Preferably, the reaction is carried out in a mixture dichloromethane/acetone (ratio 10/3 v/v). Ethyl acetate, acetone and N,N-dimethylformamide can also advantageously be used.

When IBX is used to oxidise 3 to 4, a very polar reaction environment is necessary because of the low solubility of the reagent in apolar organic solvents. The oxidation reaction is preferably performed using from 3 to 12, preferably 8.4, moles of MX for one mole of 3, in a solvent selected from the group consisting of dimethylsulfoxide, amides among which preferably N,N-dimethylformamide, cyclic ethers among which preferably tetrahydrofuran or methyltetrahydrofuran. Binary mixtures of these solvents can be used, too.

The reaction is generally performed at a temperature between about 15° C. and about 70° C.; at temperatures higher than about 70° C. the formation of relevant amounts of an impurity identified as a C1-C2 unsaturated derivative of Drospirenone 5 is observed.

In the final step c), compound 4 undergoes an acidic treatment in an organic solvent to effect elimination of water from positions C4-C5, thus yielding Drospirenone 5 which is isolated by aqueous workup. The reaction is preferably carried out with p-toluenesulfonic acid in ethyl acetate at a temperature between 0° C. and 25° C.

According to the second embodiment the process for the preparation of Drospirenone 5 from a compound of formula 2 involves the following steps:

a') removal of the hydroxyl protective group of the compound of formula 2 as above defined to give 17α-(3-hydroxypropyl)-6β,7β,15β,16β-dimethylen-5β-androstane-3β,5,17β-triol of formula 3

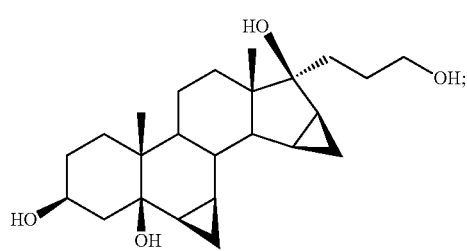

b') reaction of the compound of formula 3 with the oxidizing agent DCCA, or an alkaline metal salt thereof, in the presence of an acid with concomitant elimination of water from the positions C4-C5 to afford directly Drospirenone 5.

The process according to the second embodiment is summarised in the following Scheme 2:

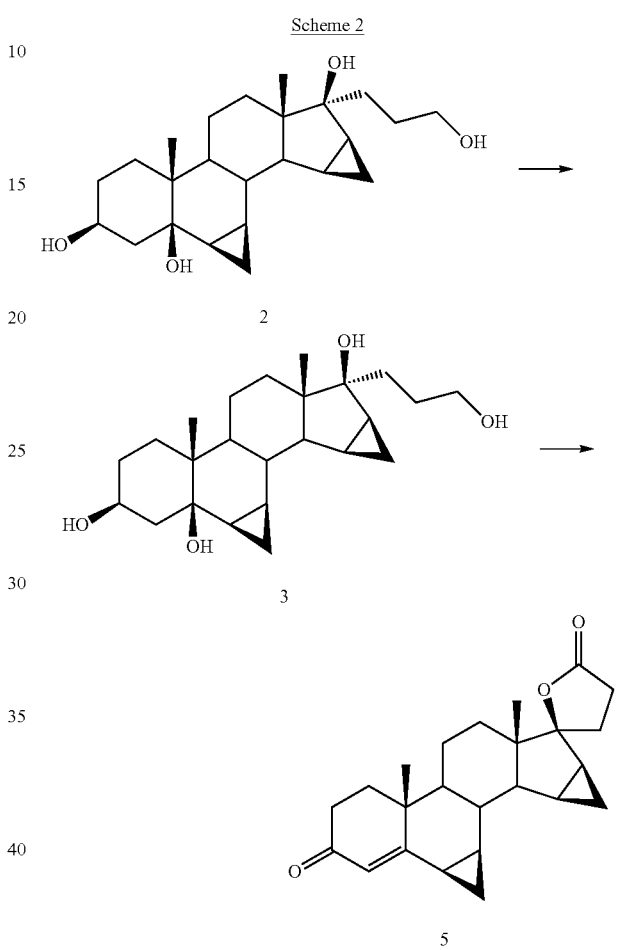

In the initial step a') compound 2 is deprotected to afford compound 3, i.e. 17α-(3-hydroxypropyl)-6β,7β,15β,16β-dimethylen-5β-androstane-3β,5,17β-triol.

In the step b') wherein DCCA, or an alkaline salt thereof, is used as the oxidant in the presence of an acid, compound 3 is converted in a single step in Drospirenone 5. DCCA sodium salt dihydrate is the preferred oxidant. The process is preferably performed in an organic solvent chosen among ketones, esters, amides, chlorinated solvents or mixtures thereof in the presence of water between 10% and 50% v/v of the organic solvent, at a temperature between about 0° C. and about 30° C., preferably at 1.8-20° C. The molar ratio of oxidizing agent and starting material is between 1 and 4, more preferably the ratio is 1.6 moles of DCCA sodium salt dihydrate for 1 mole of 3. Hydrochloric acid is preferably used in an amount between 0.5 and 4 moles per 1 mole of 3, more preferably 1.1 mole of acid for 1 mole of 3.

When R is —Si(CH$_3$)$_2$[C(CH$_3$)$_3$] (compound 2b), or any acid labile silyl group, the process of this embodiment can be performed in one single step from compound 2b to Drospirenone 5 without previously removing the sityl group. The removal of the protecting group R, the oxidation reaction and the elimination of water from positions C4-C5 take place at the same time when the acid is added to the reaction mixture.

According to the third embodiment of the invention, the process for the preparation of Drospirenone 5 from a compound of formula 2 involves the following sequential steps: a")-d"):

a") reaction of a compound of formula 2 with an oxidizing agent selected from TCCA or IBX to give a compound of formula 6

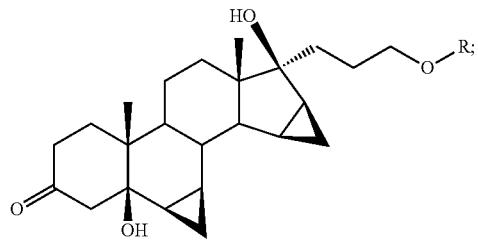

6 wherein R is selected from the group consisting of a silyl derivative $Q_3Si$—, wherein each Q, independently from one another, represents $(C_1-C_6)$alkyl, $(C_6-C_{10})$aryl, $(C_1-C_4)$alkylaryl or $(C_1-C_4)$alkoxyaryl;

b") removal of the hydroxyl protective group from the compound obtained in step a"), whereby compound 7 is obtained

7 c") reaction of compound 7 with an oxidizing agent selected from TCCA or IBX to give the compound of formula 4

4 d") elimination of water from the positions C4-C5 of compound 4, whereby Drospirenone 5 is obtained.

The process according to this third embodiment is summarised in the following Scheme 3:

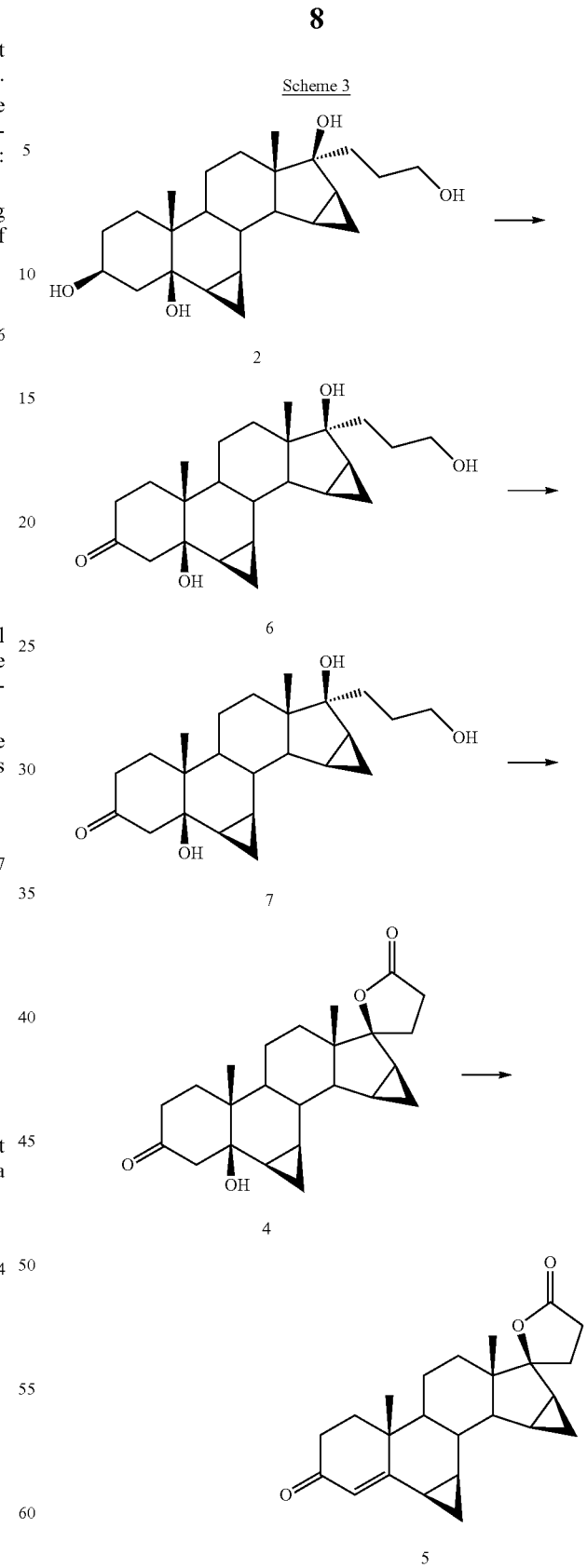

In step a"), the protected compound 2 is oxidised at the 3-position to give compound 6 using either TCCA or IBX in a suitable organic solvent.

In a preferred method of practicing this embodiment the hydroxyl protective group of compound 2 is the tert-butyldimethylsilyl group —Si(CH$_3$)$_2$[C(CH$_3$)$_3$].

When TCCA is used as the oxidant, the solvent is chosen among ketones, esters, amides, and chlorinated solvents and the reaction is performed at a temperature comprised between about 0° C. and about 70° C. using from 0.3 to 2, preferably 0.67 moles of TCCA for one mole of 2. The oxidation reaction takes place in the presence of a base, generally an amine, preferably pyridine, in an amount of 0.5 to 4 moles, more preferably 1.8 moles, for one mole of compound 2. The reaction is preferably carried out in a mixture of dichloromethane and acetone (ratio 10/1 v/v).

When in step a") IBX is used as an oxidant, the oxidation reaction is preferably performed in a solvent selected from the group consisting of dimethylsulfoxide, amides, cyclic ethers or binary mixtures thereof. Dimethylsulfoxide, dimethylformamide, tetrahydrofuran or a binary mixture of these solvents are preferably used. The reaction is generally performed at a temperature between about 15° C. and about 70° C., preferably at a temperature of about 25° C., using from 1 to 4, preferably 1.6 moles of IBX for one mole of 2.

After oxidation with TCCA or IBX compound 6 is isolated and subsequently treated in step b") with a reagent suitable for the removal of the silyl groups, to provide compound 7.

In a preferred method of practicing this embodiment, wherein compound 6 is protected as the tert-butyldimethylsilyl derivative (compound 6b), deprotection is performed with tetrabutylammonium fluoride in tetrahydrofuran whereby the deprotected compound 7 is obtained.

In step c"), a second oxidation of compound 7 with TCCA or IBX affords compound 4.

When TCCA is used the reaction is performed using from 0.3 to 3 moles TCCA for one mole of 7 at a temperature between 15° C. and 50° C., preferably using 1 mole of TCCA for 1 mole of 7 at 20° C. The oxidation reaction takes place in the presence of a base, generally an amine, preferably pyridine, in an amount of 1 to 5 moles for one mole of compound 7, more preferably 3.4 moles. The reaction is preferably carried out in a mixture of dichloromethane and acetone (ratio 10/1 v/v).

When the second oxidation is carried out with IBX, the reaction is preferably performed at a temperature between about 25° C. and about 45° C. whereby a mixture of compounds 4 and 5 is obtained. The reaction is performed using from 1 to 4 moles, preferably 3 moles of IBX for one mole of 7.

In step d") compound 4 or a mixture of compounds 4 and 5 undergoes the same acidic treatment in an organic solvent to effect elimination of water from positions C4-C5 as described for step c), whereby Drospirenone 5 is obtained.

In another preferred method of practicing this embodiment, TCCA is used in both step a") and step e").

In still another preferred method of practicing this embodiment, IBX is used in both step a") and step c").

When a compound of formula 2 wherein R=Si(CH$_3$)$_2$[C(CH$_3$)$_3$] is used as starting material in the process comprising steps a")-d"), the total yield of Drospirenone 5 from compound 2 is about 52% using TCCA and about 47% using IBX.

Drospirenone 5 obtained through the above processes can be purified by crystallization from an organic solvent, preferably a ketone or an ether. Preferably, acetone or tert-butylmethyl ether is used. An additional portion of product 5 is recovered from processing of the mother liquors. Drospirenone is obtained with a purity (HPLC, wavelength of detection: 245 nm) higher than 99%.

The process of the invention using TCCA, DCCA sodium salt and IBX provides several advantages in comparison to those of the prior art.

1. Table summarizes the yields reported for the procedures described in EP2019114A1 where a compound 2 is involved having R=—Si(CH$_3$)$_3$ (2a) or R=—Si[C(CH$_3$)$_3$](CH$_3$)$_2$ (2b).

TABLE

| Process | Reagents/Oxidants | Total yield |
|---|---|---|
| 2a-5 | CrO$_3$/H$_2$SO$_4$ | 41% |
| 2a-5 | IBX-CrO$_3$/H$_2$SO$_4$ | 51% |
| 2b-5 | MnO$_2$-TBAF-MnO$_2$ | 18.5% |
| 2a-3-5 | TBAF-MnO$_2$ | 25% |
| 2a-5 | KMnO$_4$/H$_2$SO$_4$ | 13% |

The yield obtained by applying the procedure with TCCA as an oxidant according to the present invention performing the synthesis via compound 2a is about 74% (Example 2) and about 63% (Example 3). When the process involves compound 2b, the yield of the conversion to compound 5 is greater than 52% (Example 6, 7, 8).

When IBX is used the yield from 2a to 5 is 56% (Example 4).

When DCCA is used to oxidize compound 3, deriving from 2a, to 5 the yield is around 46% (Example 5), 2. The HPLC purity of the isolated Drospirenone according to the process of the invention is
   99.3% in case TCCA is used
   99.7% in case IBX is used.

Moreover the impurity profile obtained is improved when compared to the previously reported oxidation methods and all the impurities are easily removed from the crude product. As a consequence, a high quality level is achieved by simple crystallization from acetone.

3. Compared to the synthesis where chromium (VI)-based oxidizing agents are involved, the advantage is to use reagents with much lower toxicity.
4. No heavy metals are involved in the process with TCCA, DCCA sodium salt or IBX. This is an advantage also in comparison with oxidation with Mn(IV/VII)-based oxidants. No troublesome operations are necessary both to remove metal traces from the end product and to dispose of the wastes.
5. An additional advantage with TCCA and DCCA sodium salt is due to the fact that the salts (namely, pyridinium salts) formed during the oxidation process are easy to eliminate during the work-up by simple filtration. In this case no steroidal products remain adsorbed or incorporated in the solids. On the contrary, when chromium- or manganese-based oxidants are used, the final product could be difficult to recover.
6. TCCA, DCCA sodium salt and IBX are advantageous from the economical point of view, moreover no expensive catalysts (e.g. 2,2,6,6-tetramethyl-1-piperidinyloxy free radical or derivative thereof or ruthenium catalysts) are involved in this oxidation process.
7. In particular, TCCA and DCCA sodium salt are much easier to handle and to measure than chlorine gas or solutions of metal hypochlorites, as reported in *Organic Process & Development* 2002, 6, 384-393.
8. The by-product formed by reduction of TCCA or DCCA sodium salt is cyanuric acid, a white odorless solid which is commonly used for the stabilization of available chlorine in swimming pool water and finds many synthetic applications as an intermediate of chemical products.

Still another object of the present invention is the compound 17α-(3-hydroxypropyl)-6β,7β,15β,16β-dimethylen-5β-androstan-5,17β-ol-3-one of formula 7.

The invention is now further illustrated by the following examples.

Example 1

17α-[3-Hydroxypropyl]-6β,7β,15β,16β-dimethylenandrostan-3β,5,17β-triol (3)

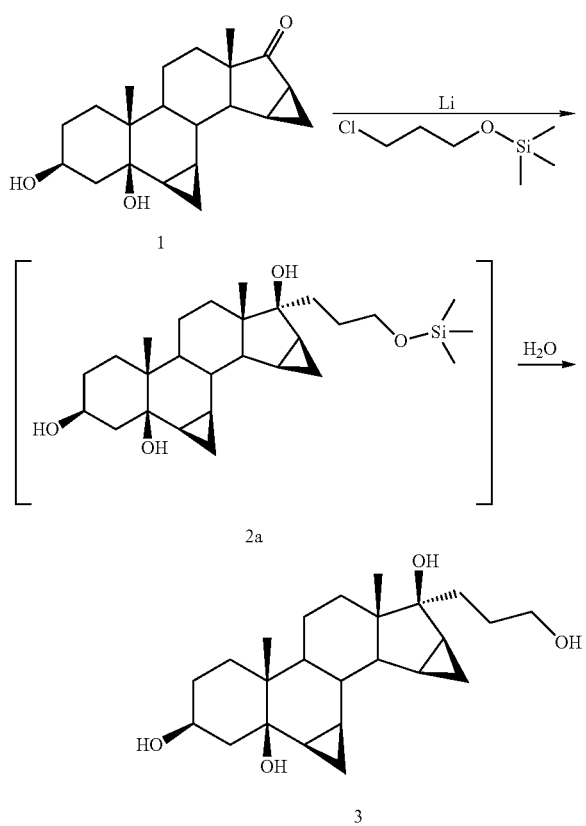

3β,5-Dihydroxy-6β,7β,15β,16β-dimethylen-5β-androst-17-one (65.00 g, 0.197 mol) is dissolved in tetrahydrofuran (2600 mL) and cooled to −15° C. under argon atmosphere. Lithium (granular, 11.2 g, 1.61 mol) is then added and stirred for 15 minutes. (3-Chloropropoxy)trimethylsilane (167.81 g, 1.007 mol) is added dropwise maintaining the temperature below 10° C. and stirring is continued at a temperature between −5 and +5° C. The reaction is monitored by TLC analysis and when no more starting material is present (about one hour), water (475 mL) is slowly added. The mixture is stirred until compound 2a is completely converted into 3, the pH value is corrected to 7-7.5 with 0.5% sulphuric acid. The two layers are separated and the aqueous one is extracted with ethyl acetate (234 mL). After separation the organic layers are washed with brine (260 mL); the inorganic layer is extracted again with ethyl acetate (234 mL) and the phases are separated. Ethyl acetate is removed at 50° C. under reduced pressure until a volume of 60 mL is reached and the precipitation of the product takes place. The filtration affords the product 3 as an off-white solid (82.88 g, title 84%, corresponding to 0.178 mol, 91%) which is used in the subsequent step without further purification.

A sample purified by crystallization is analyzed.

$^1$H-NMR {400 MHz, DMSO-$d_6$, δ (ppm)}: 0.15 (m, 1H, cyclopropyl($CH_2$)); 0.45 (m, 1H, cyclopropyl($CH_2$)); 0.61-1.78 (22H); 0.76 (s, 6H, $CH_3$-19 and $CH_3$-18); 2.07 (dd, 1.2.8, 12.0 Hz, 1H, $CH_2$-4); 3.41 (m, 2H, C$\underline{H}_2$OH); 3.84 (m, 1H, C$\underline{H}$OH); 4.13 (s, 1H, OH); 435 (bs, 1H, OH); 4.38 (t, J=5.2 Hz, 1H, $CH_2$O$\underline{H}$); 4.83 (d, J=4.0 Hz, 1H, OH-3).

$^{13}$C-NMR {200 MHz, DMSO-$d_6$, δ (ppm)}: 7.9 ($CH_2$); 14.5 (CH); 15.8 (CH); 18.9 ($CH_3$); 19.4 ($CH_3$); 22.0 ($CH_2$); 22.2 (CH); 22.8 (CH); 27.2 ($CH_2$); 27.3 ($CH_2$); 27.8 ($CH_2$); 33.6 ($CH_2$); 34.2 (CH); 36.4 ($CH_2$); 40.0 (C); 42.4 (C); 43.9 ($CH_2$); 52.7 (CH); 62.1 ($CH_2$); 63.8 ($CH_2$); 66.8 (CH); 67.9 (CH); 72.8 (C); 80.8 (C).

HPLC-MS (ESI): $[(M-H_2O)+H]^+$=373; $[M+Na]^+$=413; $[2M+Na]^+$=803.

Example 2

6β,7β,15β,16β-dimethylene-3-oxo-17α-pregn-4-ene-21,17-carbolactone (Drospirenone) (5)

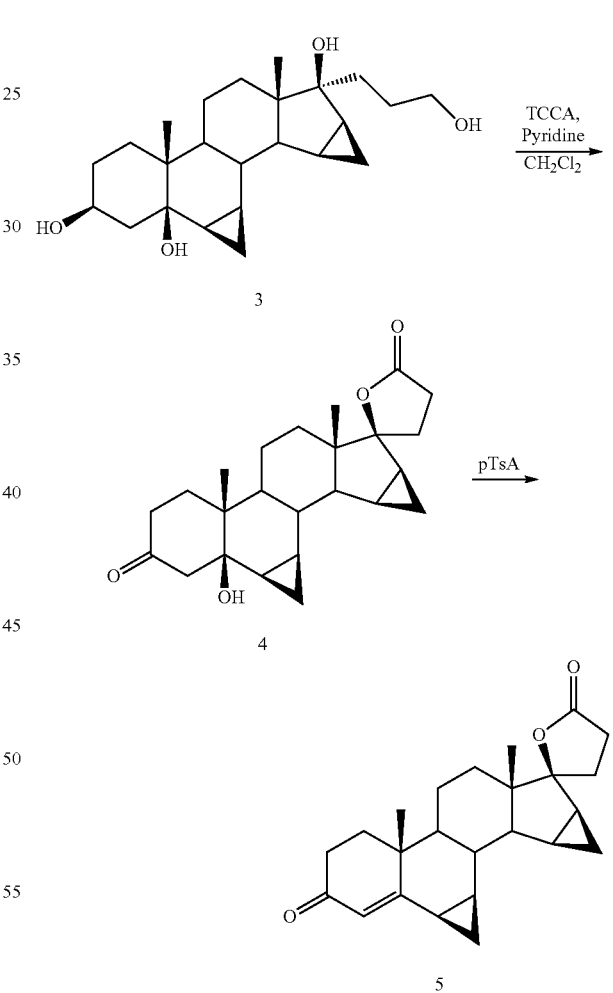

17α-(3-hydroxypropyl)-6β,7β,15β,16β-dimethylene-5β-androstan-3β,5,17β-triol 3 (30.00 g, 84% title, 0.065 mol) is suspended in dichloromethane (600 mL) at 20° C. and pyridine (37.5 mL, 0.464 mol) is added. After stirring for 10 minutes, a clear solution of trichloroisocyanuric acid (TCCA) (22.50 g, 0.097 mol) in acetone (150 mL) is added dropwise over 90 minutes at 25° C. The reaction is stirred at 25° C. for 50 minutes and monitored on TLC. After filtering the solid off and washing the cake in the filter with dichloromethane (150 mL), the collected solution is washed with water (210 mL) and saturated sodium bicarbonate solution (13 mL). The phases are separated and the aqueous one is extracted with dichloromethane (60 mL). The combined organic layers are washed first with a 10% solution of sodium metabisulfite in water (120 mL) to quench the residual oxidant and then with a 12% sulfuric acid solution (74.1 mL). The acidic phase is extracted with dichloromethane (60 mL) and the organic layers are combined with the previous ones and washed with a diluted sodium bicarbonate solution (76 mL). After separation, dichloromethane is removed from the organic phase under reduced pressure at 45° C. and the oily residue is taken up in ethyl acetate (450 mL) and cooled to 0° C. p-Toluenesulfonic acid monohydrate (5.70 g, 0.030 mol) is added and the solution is stirred for 10 minutes and allowed to reach 25° C. When the conversion to 5 is complete on TLC, the reaction mixture is washed with 5% sodium bicarbonate solution (105 mL). The aqueous phase is extracted with ethyl acetate (60 mL) and the combined organic layers are washed with water (48 mL). The concentration of the organic layers at 45° C. under reduced pressure affords the crude product as a yellow oil (35 g). The residue is crystallized from acetone and dried at 45° C. in vacuo for 16 hours (13.0 g, HPLC purity 99.3%). The mother liquors are concentrated and the residue is crystallized from acetone and dried in vacuo affording a second portion of 5 (5.1 g).

The total yield from compound 3 is 74% (0.048 mol).

$^1$H-NMR {400 MHz, CDCl$_3$, δ (ppm)}: 0.53 (1H, H-15', false q, J=8 Hz), 0.88 (1H, H-6', dt, J=10.0 Hz, 5.2 Hz), 1.00 (3H, H-18, s), 1.10 (3H, H-19, s), 1.12 (1H, H-14, m), 1.22 (1H, H-6', ddd, J=10.0, 8.4, 4.8 Hz), 1.34 (1H, H-15', m), 1.37 (1H, H-1.6, m), 1.46 (2H, H-12, m), 1.50 (1H, H-7, m), 1.59 (2H, H-11, m), 1.64 (1H, H-15, m), 1.64 (1H, H-6, m), 1.69 (1H, H-20, broad dd, J=13.4, 4.8 Hz), 1.79 (1K, H-8, dt, 1=3.6, 12.0 Hz), 1.88 (1H, H-20, ddd, J=13.4, 5.2, 2.4 Hz), 1.94 (1H, H-9, broad dd, 1=3.6, 12.0 Hz), 2.13 (1H, H-1, m), 2.40 (1H, H-21, m), 2.45 (1H, H-2, m), 2.55 (1K, H-1, m), 2.55 (1H, H-21, m), 2.64 (1H, H-2, ddd, J=17.6, 9.6, 5.2 Hz), 6.04 (1H, H-4, s).

$^{13}$C-NMR {400 MHz, CDCl$_3$, δ (ppm)}: 9.9 (C-15', CH$_2$); 16.6 (C-15, CH); 17.5 (C-19, CH$_2$); 18.8 (C-6', CH$_2$); 18.9 (C-6, CH); 19.6 (C-18, CH$_3$); 19.7 (C-7, CH); 20.8 (C-11, CH$_2$); 24.2 (C-16, CH); 29.3 (C-2, CH$_2$); 30.6 (C-1, CH$_2$); 33.9 (C-21, CH$_2$); 34.1 (C-8, CH); 36.9 (C-20, CH$_2$); 37.0 (C-12, CH$_2$); 37.3 (C-10, C); 41.5 (C-13, C); 51.5 (C-14, CH); 51.6 (C-9, CH); 96.0 (C-17, C); 125.7 (C-4, CH); 171.3 (C-5, C); 176.6 (C-22, C); 197.7 (C-3, C).

HPLC-MS (ESI): [M+H]$^+$=367; [M+Na]$^+$=389; [2M+Na]$^+$=755

Example 3

6β,7β,15β,16β-dimethylene-3-oxo-17α-pregn-4-ene-21,17-carbolactone (Drospirenone) (5)

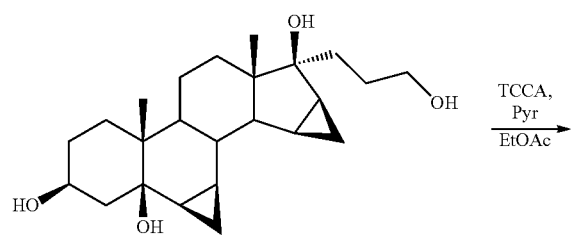

3

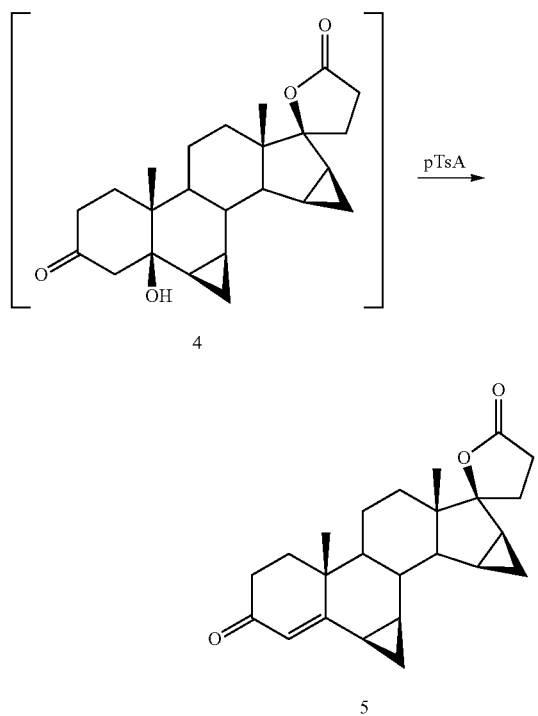

4

5

17α-(3-hydroxypropyl)-6β,7β,15β,16β-dimethylene-5β-androstan-3β,5,17β-triol 3 (1.4.50 g, 84% title, 0.031 mol) is suspended in ethyl acetate (300 mL) at 18-24° C. and pyridine (18.90 mL, 0.234 mol) is added. After stirring for 10 minutes, a clear solution of trichloroisocyanuric acid (TCCA, 11.25 g, 0.048 mol) in acetone (90 mL) is added dropwise over 90 minutes at 25° C. The reaction is stirred at 25° C. for 3 hours, monitoring the conversion by TLC. After filtering the solid off and washing the cake in the filter with ethyl acetate (50 mL), the collected solution is washed with a sodium metabisulfite solution (0.03%, 30 mL) to quench the residual oxidant. After separation the inorganic phase is extracted with ethyl acetate (10 mL). The combined organic layers are washed with a 15% sulphuric acid solution (80 mL). The layers are stirred for 30 minutes and then separated. The acidic phase is extracted with ethyl acetate (100 mL) and the organic layers are combined and cooled to 0° C. p-Toluenesulfonic acid monohydrate (6.00 g, 0.032 mol) is added and the mixture is stirred for 2 hours. A saturated sodium bicarbonate solution (50 mL) and water (50 mL) are added, the layers are stirred and then separated. The aqueous phase is extracted twice with ethyl acetate (2×50 mL) and after separation the organic phases are combined and concentrated under reduced pressure at 45° C. The crude product is crystallized from acetone affording a colourless solid (5.95 g, 0.016 mol).

By crystallization of the residue from the mother liquors a second portion of product is obtained (1.2 g, 0.003 mol). (Total yield 63%).

Analytical data correspond to the ones obtained in Example 2.

Example 4

6β,7β,15β,16β-Dimethylen-3-oxo-17α-pregn-4-ene-21,17-carbolactone (Drospirenone) (5),

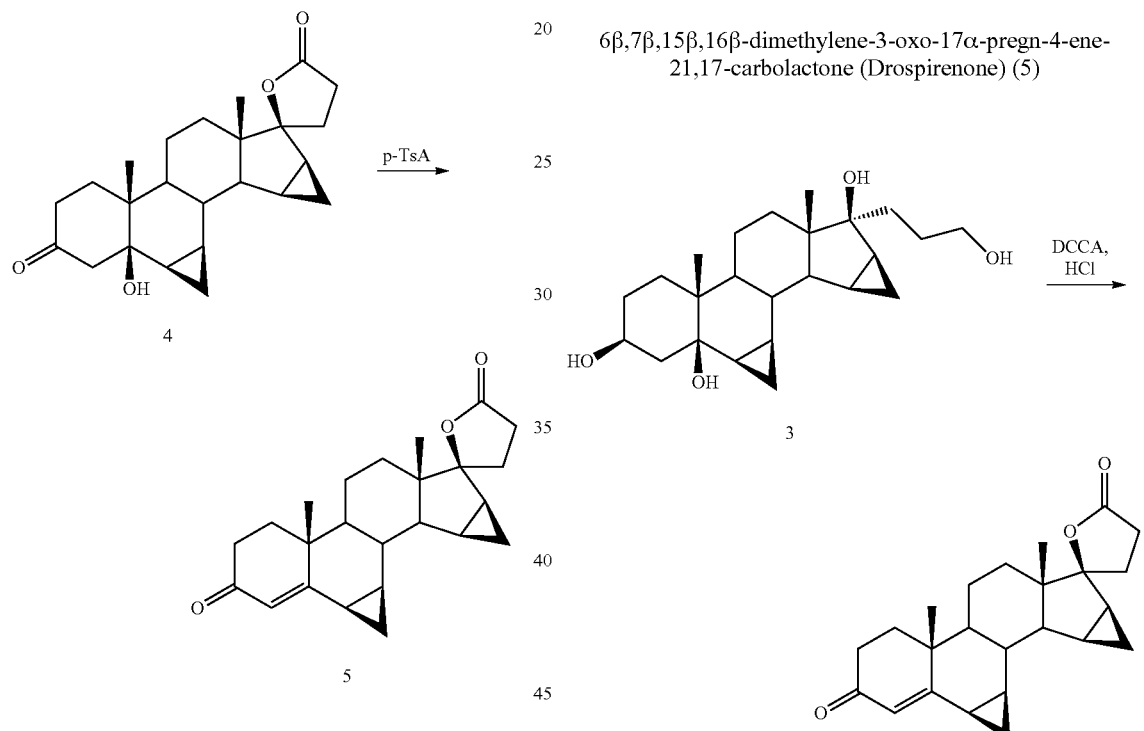

17α-(3-hydroxypropyl)-6β,7β,15β,16β-dimethylene-5β-androstan-3β,5,17β-triol 3 (17.40 g, 84% title, 0.037 mol) is dissolved in N,N-dimethylformamide (280.0 mL) and dimethylsulfoxide (10.0 mL) at 20° C. IBX (58.6 g, 0.209 mol) is added and the reaction is stirred overnight. A second portion of IBX (29.0 g, 0.104 mol) is added and stirring is continued for 2 hours at 60° C. The mixture is then cooled to 0° C. and filtered on a glass filter washing the solid with tetrahydrofuran (3×100 mL). Water (200 mL) is added (1200 mL) to the filtrate and the mixture is stirred at 0° C. for two hours. A first portion of crude product is obtained by filtration washing the solid in the filter with water (100 mL). The solid is a mixture of compounds 4 and 5 (3.70 g of compound 4 and 2.27 g of 5, 0.016 mol) which is then stirred in ethyl acetate (135 L) and treated with p-toluenesulfortic acid monohydrate (3.40 g, 0.018 mol). The mixture is stirred first at 0° C. for 30 minutes and then at 20° C. for 2 hours until the starting material is no more detectable on TLC. The solution is washed with saturated sodium bicarbonate solution (50 mL) and the aqueous phase is extracted with ethyl acetate (3×100 mL). The removal of the organic solvent under reduced pressure affords an oil which is taken up in acetone (10 mL), cooled to 0° C. and stirred for one hour. After filtration the crude product is crystallized to afford the title compound 5 (4.4 g, 0.012 mol, HPLC purity 99.7%).

From the mother liquors of the first solid containing 4 and 5 an additional portion of products is recovered by extraction with methylene chloride and removal of the solvent under reduced pressure affording an oily residue containing 3.29 g of compound 4 and 1.92 g of 5 (total 0.014 mol). By treatment with p-toluenesulfonic acid monohydrate in ethyl acetate and subsequent isolation, a second portion of the title compound 5 is obtained (3.39 g, 0.009 mol). (Total yield; 56%).

Analytical data are in agreement with the ones reported in Example 2.

Example 5

6β,7β,15β,16β-dimethylene-3-oxo-17α-pregn-4-ene-21,17-carbolactone (Drospirenone) (5)

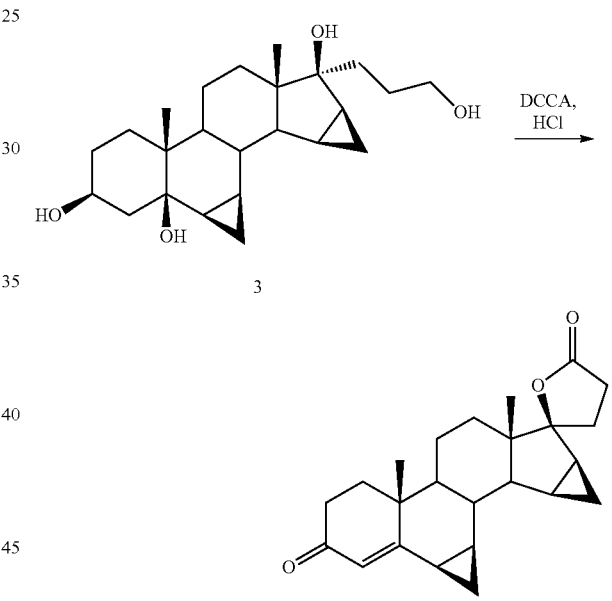

17α-(3-hydroxypropyl)-6β,7β,15β,16β-dimethylene-5β-androstan-3β,5,17β-triol 3 (8.00 g, title 84%, 0.017 mol) is suspended in acetone (120 mL) at 20° C. A solution of sodium dichloroisocyanurate sodium salt dihydrate (DCCA, 7.5 g, 0.029 mol) in water (80.0 mL) is added dropwise maintaining the temperature at 18-22° C. A 6N hydrochloric acid solution (3.3 mL, 0.020 mol) is added dropwise. The reaction is stirred for 2 hours, monitoring the conversion by TLC. The mixture is then filtered and the panel is washed with acetone (50 mL). The filtrate washed twice with sodium bicarbonate solution (20 mL, 15 mL). After separation the aqueous phase is extracted with ethyl acetate (20 mL). The combined organic layers are concentrated under reduced pressure at 45° C. and the residue is crystallized from acetone and dried at 45° C. for 16 hours. Product 5 is obtained as a colorless solid (3.01 g, 0.008 mmol, HPLC purity 96:1%, 46%).

Analytical data correspond to the ones obtained in Example 2.

Example 6

17α-[3-(tert-Butyl-dimethylsilanyloxy)propyl]-6β,7β,15β,16β-dimethylen-5β-androstan-5,17β-ol-3-one (6b)

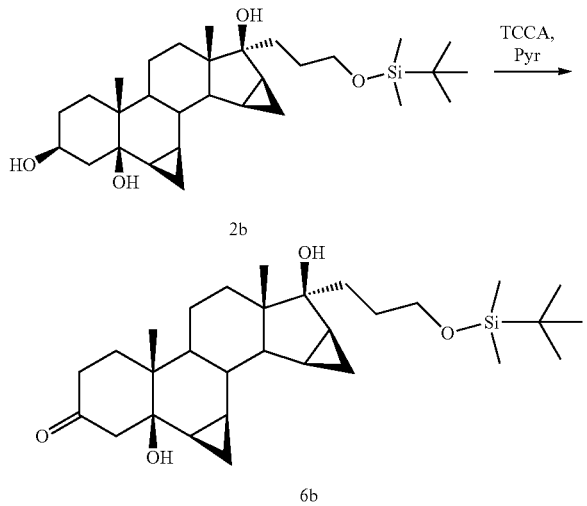

17α-[3-(tert-Butyldimethylsilanyloxy)propyl]-6β,7β,15β,16β-dimethylen-5β-androstane-3β,5,17β-triol 2b prepared according to EP2019114A1 (6.00 g, 0.012 mol) is dissolved in dichloromethane (60.0 mL) at 25° C. and pyridine (1.8 mL, 1.76 g, 0.022 mol) is added. A solution of trichloroisocyanuric acid (1.80 g, 0.008 mol) in acetone (6.0 mL) is added and after few minutes some precipitate is formed. The reaction is checked by TLC analysis and no more starting material is detected showing that the oxidation process is complete. The solids are filtered off and washed with dichloromethane (30.0 mL). The filtrate is washed twice with 10% sodium hydrogen sulfite solution (2×50 mL), once with 5% sodium hydrogen sulfate solution (50 mL) and brine (30 mL). The mixed aqueous phases are acidified to pH=1 with sulphuric acid and extracted with dichloromethane (50 mL). The organic phases are combined and washed with saturated sodium bicarbonate solution (20 mL). The organic solution is concentrated under reduced pressure at 40° C. and the title compound is obtained as a yellow foam (5.8 g, 0.012 mol, 97%) and is used in the subsequent step without further purification.

$^1$H-NMR {400 MHz, CDCl$_3$, δ (ppm)}: 0.64-2.21 (m, 21H) 0.04 (s, 6H, Si(CH$_3$)$_2$); 0.17 (m, 1H, cyclopropyl); 0.54 (m, 1H, cyclopropyl); 0.79 (s, 3H, CH$_3$-18); 0.80 (s, 3H, CH$_3$-19); 0.87 (s, 9H, C(CH$_3$)$_3$); 2.24 (d, J=15.4 Hz, 1H, H-4); 2.97 (d, J=15.4 Hz, 1H, H-4); 3.6 (m, 2H, CH$_2$—O—Si); 4.17 (s, 1H, OH); 4.56 (s, 1H, OH).

$^{13}$C-NMR {-400 MHz, DMSO-d$_6$, δ (ppm)}: −5.2 (2×CH$_3$); 7.9 (CH$_2$); 12.0 (CH$_2$); 15.5 (CH); 15.6 (CH); 17.5 (C); 17.9 (CH$_3$); 19.3 (CH$_3$); 21.7 (CH$_2$); 22.6 (CH); 24.3 (CH); 25.8 (3×CH$_3$); 27.3 (CH$_2$); 33.2 (CH$_2$); 33.8 (CH$_2$); 34.2 (CH); 36.1 (CH$_2$); 36.3 (CH$_2$); 39.6 (C); 42.4 (C); 45.8 (CH); 52.4 (CH); 53.8 (CH$_2$); 63.7 (CH$_2$); 75.2 (C); 80.6 (C); 210.2 (C).

HPLC-IV (ESI): [M−H$_2$O+H]$^+$=485, [M+Na]$^+$=525, [2M+Na]$^+$=1027

Example 7

17α-(3-Hydroxypropyl)-6β,7β,15β,16β-dimethylen-5β-androstan-5,17β-ol-3-one (7)

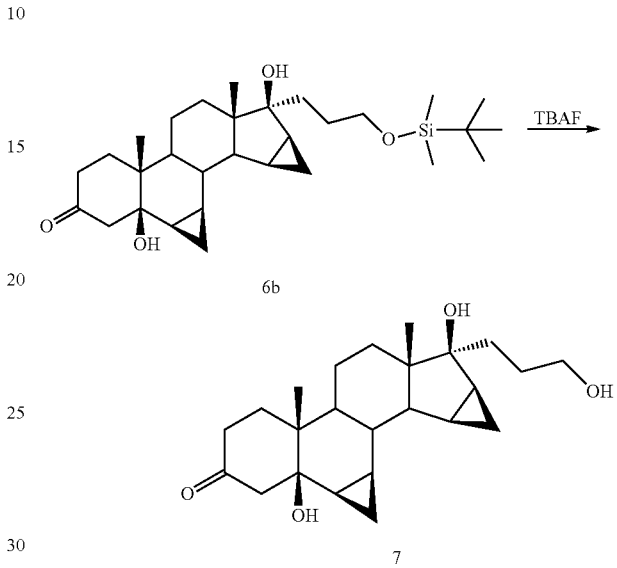

A solution of 17α-[3-(tert-butyldimethylsilanyloxy)propyl]-6β,7β,15β,16β-dimethylen-5β-androstan-5,17β-ol-3-one 6b obtained according to Example 6 (5.8 g, 0.012 mol) in tetrahydrofuran (50 mL) is treated at 0° C. with tetra-n-butylammonium fluoride trihydrate (1.8 g, 0.006 mol). After stirring for three hours no more starting material is visible on TLC and the mixture is diluted with ethyl acetate (50 mL) and washed with saturated sodium bicarbonate solution (50 mL). After separation the aqueous phase is extracted with ethyl acetate (30 mL) and the combined organic layers are washed with brine (30 mL). The organic solvents of the upper phase are removed under reduced pressure at 45° C. and the residue is taken up in ethyl acetate (15 mL). After stirring at 0° C. for 30 minutes the product is isolated by filtration and washed with ethyl acetate (5 mL). Compound 7 is obtained as an off-white solid (3.4 g, 0.009 mol, 76%).

$^1$H-NMR {400 MHz, CDCl$_3$, δ (ppm)}: 1.97-1.22 (16H); 0.35 (m, 1H, H-cyclopropyl); 0.71 (m, 1H, H-cyclopropyl); 0.91 (m, 1H); 0.94 (s, 6H, CH$_3$-18+ CH$_3$-19); 1.09 (m, 1H); 2.08 (bs, 1H, OH); 2.22 (ddd, J=4.4 Hz, 10.0 Hz, 15.2 Hz); 2.35 (dddd, 1=1.6, 4.0, 8.0, 1.5.2 Hz, 1H, H-2); 2.48 (dd, J=1.6, 15.2 Hz, 1H, H-4); 2.98 (d, J=15.2 Hz, 1H, H-4); 3.75 (m, 2H, CH$_2$OH).

$^{13}$C-NMR {400 MHz, DMSO-d$_6$, δ (ppm)}: 8.3 (CH$_2$); 12.5 (CH$_2$); 15.9 (CH); 16.0 (CH); 18.0 (CH$_3$); 19.8 (CH$_3$); 22.1 (CH$_2$); 22.7 (CH); 24.8 (CH); 27.7 (CH$_2$); 34.1 (CH$_2$); 34.2 (CH$_2$); 34.6 (CH); 36.5 (CH$_2$); 36.6 (CH$_2$); 39.7 (C); 42.4 (C); 45.6 (CH); 52.2 (CH); 53.8 (CH$_2$); 62.0 (CH$_2$); 75.3 (C); 80.7 (C); 210.3 (C).

HPLC-MS (EST): [M−H$_2$O+H]$^+$=371, [M+Na]$^+$=411, [2M+Na]$^+$=799

Example 8

6β,7β,15β,16β-Dimethylen-3-oxo-17α-pregn-4-ene-21,17-carbolactone (Drospirenone) (5)

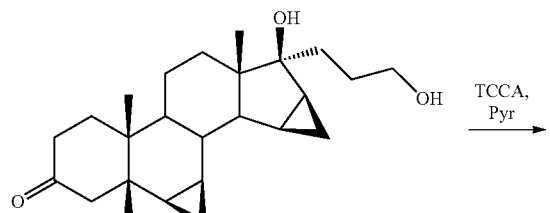

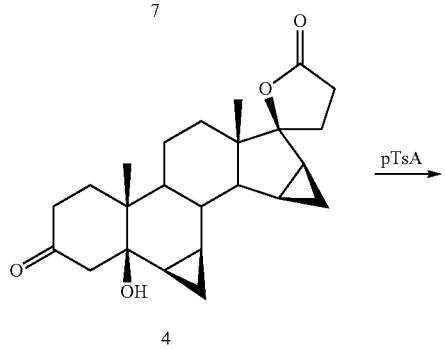

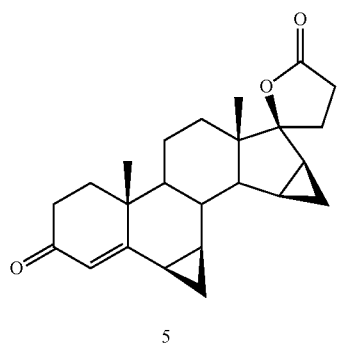

17α-(3-Hydroxypropyl)-6β,7β,15β,16β-dimethylen-5β-androstan-5,17β-ol-3-one 7 obtained according to Example 7 (3.3 g, 0.009 mol) is dissolved in dichloromethane (60 nip and pyridine (2.5 mL, 0.031 mol) at 20° C. and a solution of TCCA (2.0 g, 0.009 mol) in acetone (6.0 mL) is added. The mixture is stirred at 20° C. and after 3.5 hours TLC analysis shows that the conversion to compound 4 is complete. The suspension is then filtered and a solution is collected which is washed twice with 7% sodium bisulfite solution (2×50 mL), once with 5% sodium bisulfate solution (50 mL) and with brine (50 mL). The organic phase is concentrated under reduced pressure and the residue is dissolved in ethyl acetate (30 mL). By treatment with p-toluenesulfonic acid monohydrate. (0.40 g, 0.002 mol) first at 0° C. and then at 25° C. for one hour the formation of Drospirenone is complete. The mixture is washed with a saturated sodium bicarbonate solution (30 mL) and with brine (10 mL). The organic phase is concentrated under reduced pressure affording the crude product 5 (3.4 g). The solid is crystallized from acetone (10 mL) obtaining a first portion of 5 (1.20 g, 0.003 mol, HPLC purity 99.3%). The mother liquors are concentrated and the residue is crystallized from tert-butylmethylether (7.0 mL). After filtration a second crop of 5 is obtained (1.0 g, 0.003 mol, HPLC purity 97.5%). (Total yield: 0.006 mol, 70%).

Analytical data are in agreement with the ones reported in Example 2.

Example 9

17α-[3-(tert-Butyl-dimethylsilanyloxy)propyl]-6β,7β,15β,16β-dimethylen-5β-androstan-5,17β-ol-3-one (6b)

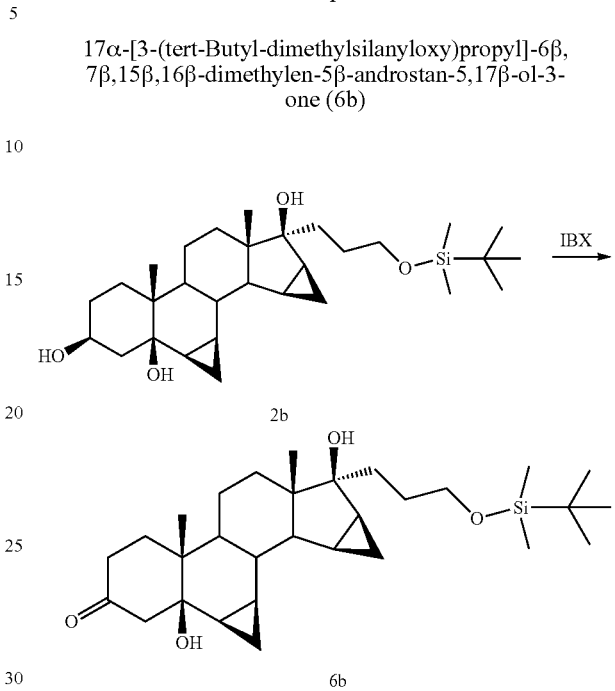

2-Iodoxybenzoic acid (4.4 g, 0.016 mol) is suspended in dimethylsulfoxide (20.0 mL) at 25° C. and 17α-[3-(tert-butyldimethylsilanyloxy)propyl]-6β,7β,15β,16β-dimethylen-5β-androstane-3β,5,17β-triol 2b prepared according to EP2019114A1 (5.0 g, 0.010 mol) is added. After 3-4 minutes the mixture turns into a clear solution which turns again into a suspension two hours later. When TLC analysis reveals that no more starting material is present, water (50 mL) is added followed by ethyl acetate (50 mL). The solids are filtered off and washed with water and ethyl acetate; the two layers of the filtrate are separated. The aqueous phase is extracted with ethyl acetate (50 mL) and the phases are separated. The combined organic phases are washed with water (50 mL) and brine (30 mL) and concentrated under reduced pressure at 45° C. to yield compound 6b (5.8 g, 0.012 mol, 73%).

Analytical data correspond to the ones reported in Example 6.

Example 10

17α-(3-hydroxypropyl)-6β,7β,15β,16β-dimethylen-5β-androstan-5,17β-ol-3-one (7)

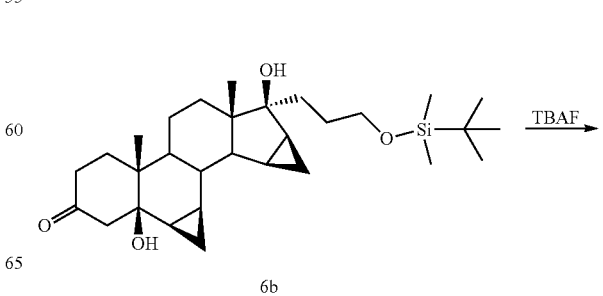

-continued

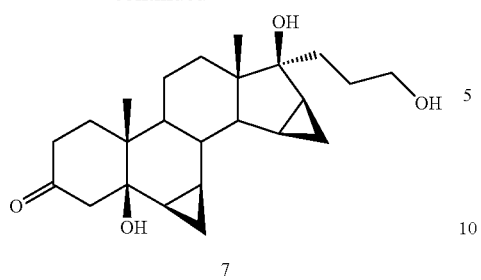

7

17α-[3-(tert-Butyl-dimethylsilanyloxy)propyl]-6β,7β, 15β,16β-dimethylen-5β-androstan-5,17β-ol-3-one 6b obtained according to Example 9 (5.5 g, 0.011 mol) is dissolved in tetrahydrofuran and cooled to 0° C. Tetrabutylammonium fluoride trihydrate is added in three portions (1.74 g, 0.006 mol) over 2 hours; the mixture is then stirred at 0° C. for two additional hours and analyzed by TLC. After allowing the reaction to reach room temperature, ethyl acetate (50 mL) and saturated sodium bicarbonate solution (50 mL) are added and the phases are separated. The aqueous layer is extracted with ethyl acetate (30 mL) and the combined organic phases are washed with brine (50 mL). After separation the organic solvent is removed under reduced pressure at 45° C. affording the product 7 as a pale yellow solid (5.4 g, quantitative) which is used in the following step without further purification.

Analytical data correspond to the ones reported in Example 7.

Example 11

6β,7β,15β,16β-Dimethylen-3-oxo-17α-pregn-4-ene-21,17-carbolactone (Drospirenone) (5)

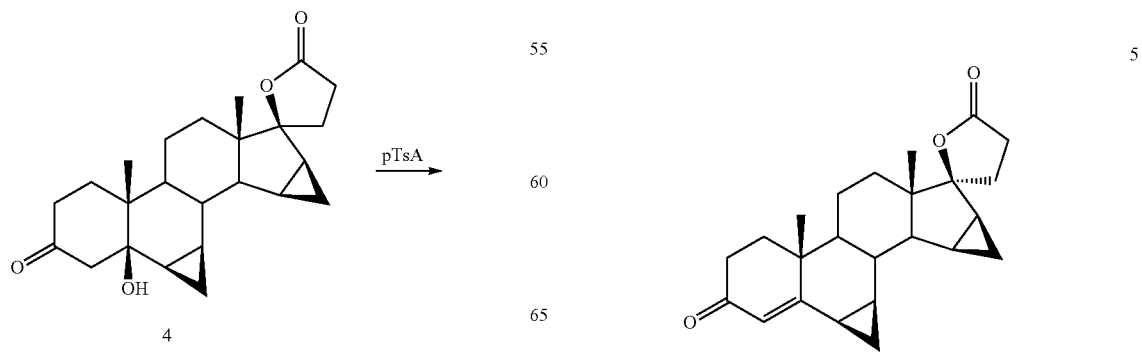

-continued

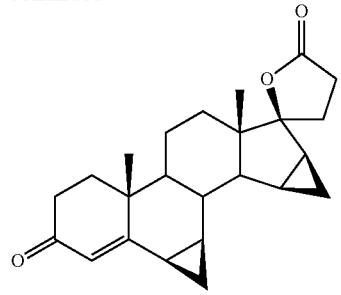

5

A suspension of IBX (8.5 g, 0.030 mol) in dimethylsulfoxide (50.0 nit) is added to 17α-(3-hydroxypropyl)-6β,7β,15β,16β-dimethylen-5β-androstan-5,17β-ol-3-one 7 obtained according to Example 10 (5.2 g, 0.010 mol) at 25° C. and the reaction is stirred for 1.5 hours. The temperature is then raised to 45° C. and stirring is continued overnight.

The mixture is allowed to reach room temperature, when ethyl acetate (100 mL) and water (100 mL) are added. After filtering the salts off and washing the solid with ethyl acetate and water, the collected layers are separated. The organic phase is washed with water (50 mL) and brine (30 mL) and the combined aqueous phases are extracted with ethyl acetate (10 mL). The organic layers are concentrated under reduced pressure at 45° C. affording a residue containing a mixture of 4 and 5 which is dissolved in ethyl acetate (50 mL). p-Toluenesulfonic acid monohydrate (0.50 g, 0.003 mol) is then added at 0° C., and the mixture is allowed to reach 25° C. After 30 minutes the formation of Drospirenone 5 is complete and the mixture is washed with saturated sodium bicarbonate solution (30 nip. The aqueous phases are extracted with ethyl acetate (2×20 mL); after separation the organic layers are washed with brine (20 mL) and concentrated under reduced pressure at 45° C. The crude product is taken up with tert-butylmethyl ether (10 mL) at 50° C. under stirring and then cooled to room temperature. After stirring overnight, the system is cooled to 0-5° C. and the precipitate is filtered off. The solid in the filter is washed with tert-butylmethyl ether (5.0 mL) and then allowed to dry overnight at room temperature (2.4 g, 0.007 mol, HPLC purity 94.5%, 65%).

The analytical results are in agreement with those reported in Example 2.

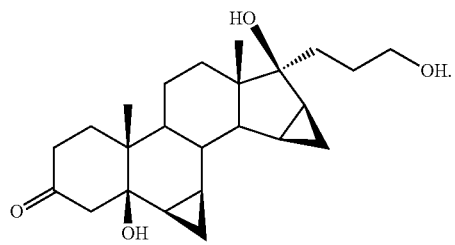

The invention claimed is:
1. Process for the preparation of 6β,7β,15β,16β-dimethylen-3-oxo-17α-pregn-4-ene-21,17-carbolactone (Drospirenone, 5)

from a compound of formula 2

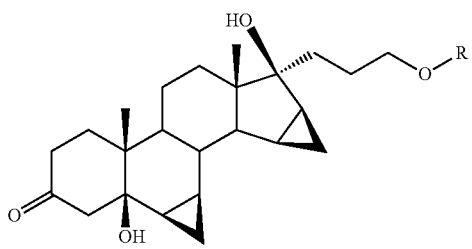

wherein R is a hydroxyl protective group selected from the group consisting of a silyl derivative $Q_3Si-$, wherein each Q, independently from one another, represents ($C_1$-$C_6$)alkyl, ($C_6$-$C_{10}$)aryl, ($C_1$-$C_4$)alkylaryl or ($C_1$-$C_4$)alkoxyaryl, said process comprising the following sequential steps a)-c):

a) removing the hydroxyl protective group of the compound of formula 2 to give compound 17α-(3-hydroxypropyl)-6β,7β,15β,16β-dimethylen-5β-androstane-3β,5,17β-triol of formula 3

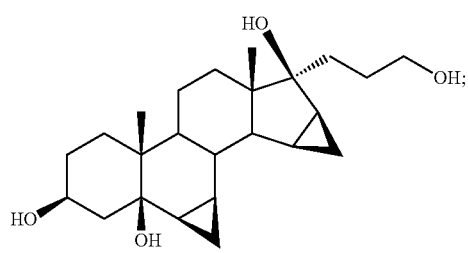

b) reacting the compound of formula 3 with an oxidizing agent selected from 1,3,5-trichloro-1,3,5-triazine-2,4,6-(1H,3H,5H)-trione (TCCA) in the presence of a base or with 1-hydroxy-1,2-benziodoxol-3(1H)-one 1-oxide (IBX) to give a compound of formula 4

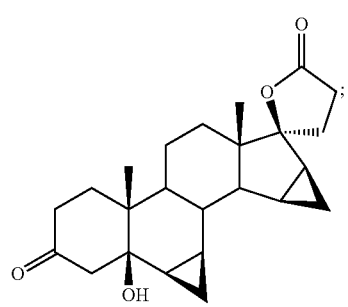

c) eliminating water from positions C4-C5 of the compound 4, whereby Drospirenone 5 is obtained;
or the following sequential steps a')-b'):
a') removing the hydroxyl protective group of the compound of formula 2 as above defined to give the 17α-(3-hydroxypropyl)-6β,7β,15β,16β-dimethylen-5β-androstane-3β,5,17β-triol of formula 3

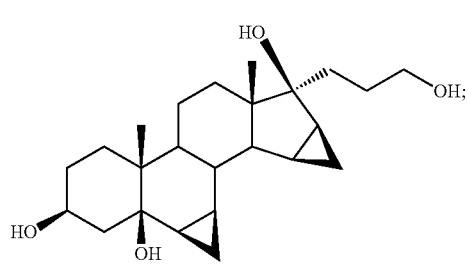

b') reacting the compound of formula 3 with the oxidizing agent 1,3-dichloro-1,3,5-triazine-2,4,6-(1H,3H,5H)-trione (DCCA), or an alkaline metal salt thereof, in the presence of an acid with concomitant elimination of water from the positions C4-C5 to afford Drospirenone 5;
or the following sequential steps a")-d"):
a") reacting a compound of formula 2 with an oxidizing agent selected from TCCA or IBX to give a compound of formula 6

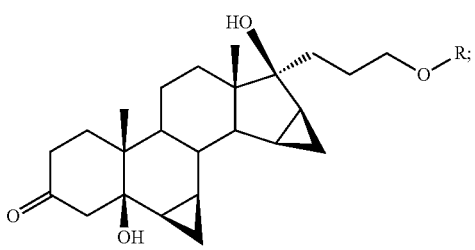

wherein R is selected from the group consisting of a silyl derivative $Q_3Si-$, wherein each Q, independently from one another, represents ($C_1$-$C_6$)alkyl, ($C_6$-$C_{10}$)aryl, ($C_1$-$C_4$)alkylaryl or ($C_1$-$C_4$)alkoxyaryl;

b") removing the hydroxyl protective group from the compound obtained in step a"), whereby compound 7 is obtained

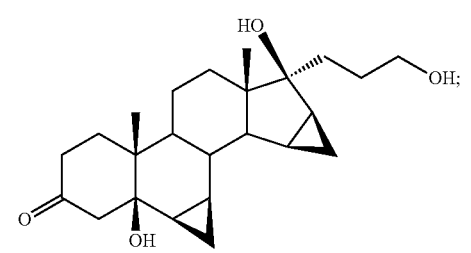

c") reacting compound 7 with an oxidizing agent selected from TCCA or IBX to give the compound of formula 4

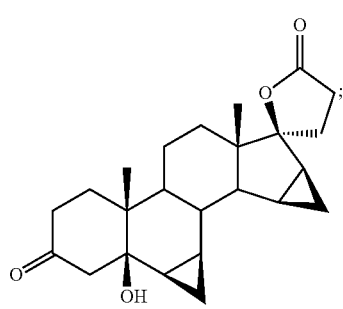

d") eliminating water from the positions C4-C5 of compound 4, whereby Drospirenone 5 is obtained.

2. The process of claim 1 wherein the hydroxyl protective group is a silyl derivative selected from the group of —Si(CH$_3$)$_3$ or Si(CH$_3$)$_2$[C(CH$_3$)$_3$].

3. The process of claim 1 wherein in step a) or a') the hydroxyl protective group is —Si(CH$_3$)$_3$.

4. The process of claim 1 wherein in step a) or a'), or a") and b") the hydroxyl protective group is —Si(CH$_3$)$_2$[C(CH$_3$)$_3$].

5. The process according to claim 1 wherein in step b) or in steps a") and c") the oxidizing agent is TCCA.

6. The process according to claim 1 wherein in step b) or in steps a") and c") the oxidizing agent is IBX.

7. The process according to claim 1 wherein in step b') DCCA sodium salt dihydrate is used.

8. The process according to claim 5, wherein the oxidation is performed at a temperature between about 0° C. and about 70° C. in an organic solvent selected from ketones, esters, amides, chlorinated solvents and mixture thereof, in the presence of a base.

9. The process of claim 8 wherein the oxidation is performed in a mixture of dichloromethane and acetone and the base is pyridine.

10. The process of claim 8 wherein the oxidation is performed in ethyl acetate and the base is pyridine.

11. The process according to claim 6, wherein the oxidation is performed at a temperature between about 15° C. and about 70° C. in an organic solvent selected from dimethylsulfoxide, dimethylformamide, tetrahydrofuran and mixtures thereof.

12. The process according to claim 7 wherein the oxidation is performed in an organic solvent selected from the group consisting of ketones, esters, amides, chlorinated solvents or mixtures thereof in the presence of water in amounts between 10% and 50% v/v of the organic solvent, at a temperature between about 0° C. and about 30° C.

13. The process according to claim 1, wherein in steps c) or d") the elimination of water from the positions C4-C5 of compound 4 to give Drospirenone 5 is performed by acidic treatment in an organic solvent.

14. The process according to claim 13, wherein the acidic treatment is performed with p-toluenesulfonic acid in ethyl acetate.

15. The compound 17α-[3-hydroxypropyl]-6β,7β;15β,16β-dimethylen-5β-androstan-5,17β-ol-3-one of formula 7